US012722020B2

(12) United States Patent
Wunderl et al.

(10) Patent No.: US 12,722,020 B2
(45) Date of Patent: Sep. 1, 2026

(54) PLASMA DEVICE FOR TREATING BODY SURFACES

(71) Applicants: terraplasma GmbH, Garching (DE); terraplasma medical GmbH, Garching b. Munich (DE)

(72) Inventors: Martin Wunderl, Weßling (DE); Rico Unger, Munich (DE); Jens Kirsch, Herbertshausen (DE); Julia Zimmermann, Munich (DE)

(73) Assignees: terraplasma GmbH, Garching (DE); terraplasma medical GmbH, Garching b. Munich (DE)

( * ) Notice: Subject to any disclaimer, the term of this patent is extended or adjusted under 35 U.S.C. 154(b) by 1166 days.

(21) Appl. No.: 17/252,041

(22) PCT Filed: Jun. 13, 2019

(86) PCT No.: PCT/EP2019/065570
§ 371 (c)(1),
(2) Date: Dec. 14, 2020

(87) PCT Pub. No.: WO2019/238863
PCT Pub. Date: Dec. 19, 2019

(65) Prior Publication Data

US 2021/0260394 A1 Aug. 26, 2021

(30) Foreign Application Priority Data

Jun. 15, 2018 (DE) ........................ 102018209735.6

(51) Int. Cl.
*A61N 1/44* (2006.01)
*A61L 2/02* (2006.01)
(Continued)

(52) U.S. Cl.
CPC .................. *A61N 1/44* (2013.01); *A61L 2/02* (2013.01); *A61L 2/14* (2013.01); *A61L 2/26* (2013.01);
(Continued)

(58) Field of Classification Search
CPC .................................................... H05H 1/2406
See application file for complete search history.

(56) References Cited

U.S. PATENT DOCUMENTS

2010/0125267 A1* 5/2010 Lee ...................... A61B 18/042 315/111.21
2012/0046597 A1* 2/2012 Morfill ................. H05H 1/2406 604/20

(Continued)

FOREIGN PATENT DOCUMENTS

DE 102009028190 A1 2/2011
JP 2018-503440 A 2/2018

(Continued)

OTHER PUBLICATIONS

English translation of the International Preliminary Report on Patentability for PCT/EP2019/065570 dated Dec. 15, 2020, 6 pages.

(Continued)

*Primary Examiner* — Randy Boyer
(74) *Attorney, Agent, or Firm* — Sheppard Mullin Richter & Hampton LLP

(57) ABSTRACT

The invention relates to a plasma device (1) for treating body surfaces, comprising a main body (3) that can be held in the hand, on which a plasma source (5) is arranged, which is designed for generating a non-thermal plasma, and comprising a spacer which is designed to define, when installed, a distance between the plasma source (5) and a body surface to be treated, wherein the spacer (7) can be detachably connected to the main body (3) and/or to the plasma source
(Continued)

(5), and wherein the plasma source (5) can be detachably connected to the main body (3).

14 Claims, 5 Drawing Sheets

(51) Int. Cl.

| | |
|---|---|
| ***A61L 2/14*** | (2006.01) |
| ***A61L 2/26*** | (2006.01) |
| ***H05H 1/24*** | (2006.01) |
| *A61L 103/05* | (2026.01) |

(52) U.S. Cl.

CPC ........ *H05H 1/2439* (2021.05); *A61L 2103/05* (2026.01); *A61L 2202/11* (2013.01); *H05H 2245/34* (2021.05)

(56) References Cited

U.S. PATENT DOCUMENTS

2013/0040469 A1 2/2013 Hsu
2013/0289557 A1* 10/2013 Hancock ................ H01Q 21/06 606/33
2015/0238248 A1* 8/2015 Thompson ........... A61B 18/042 606/50
2015/0366042 A1* 12/2015 Zaidi .................... H05H 1/2406 315/111.21
2016/0106993 A1* 4/2016 Watson ................. A61M 16/12 604/23
2016/0192986 A1 7/2016 Bonn
2016/0287310 A1 10/2016 Nettesheim et al.
2017/0303381 A1 10/2017 Wang
2018/0126183 A1* 5/2018 Nijdam ................ A61N 1/0404
2019/0070407 A1 3/2019 Kim
2019/0105506 A1* 4/2019 Bourquin ............. A61N 5/0624

FOREIGN PATENT DOCUMENTS

WO WO-2016192986 A1 * 12/2016 ............. A61B 18/04
WO 2017131393 A1 8/2017
WO 2017162505 A1 9/2017

OTHER PUBLICATIONS

English translation of International Search Report and Written Opinion for PCT/EP2019/065570 dated Dec. 19, 2019, 10 pages.

* cited by examiner

PLASMA DEVICE FOR TREATING BODY SURFACES

CROSS REFERENCE TO RELATED APPLICATIONS

This application is a U.S. National Stage Application under 35 U.S.C. 371 of International Application No. PCT/EP2019/065570, filed Jun. 13, 2019, which claims priority to German Patent Application No. 10 2018 209 735.6, filed Jun. 15, 2018. The contents of each of the aforementioned are hereby incorporated by reference in their entirety into the present disclosure.

The invention relates to a plasma device for treating body surfaces.

Such a plasma device is used in particular for the sterilization and/or disinfection of body surfaces, in particular skin surfaces, and/or for wound treatment, wherein a non-thermal plasma generated by the plasma device has positive effects on wounds through its sterilizing/disinfecting properties, and also actively supports wound healing. Depending on the specific application of the plasma device, it is necessary to maintain a certain distance between a plasma source of the plasma device, i.e. a location where the plasma is generated, and the treatment location, in particular the skin surface and/or the wound. This therefore requires precise positioning of the plasma device vertically above the body treatment surface. At the same time, it must be ensured that parts of the plasma device that come into contact with the treated surface or that can otherwise become unsterile are not used to treat different wounds, and certainly not on different patients, without at least being sterilized or disinfected in between. Known plasma devices can be improved in particular in this regard.

The invention is based on the object of creating a plasma device for treating body surfaces in which the disadvantages mentioned do not occur.

The object is achieved in that a plasma device having the features of claim 1 is created. Advantageous configurations are found in the dependent claims.

The object is achieved in particular by creating a plasma device for treating body surfaces, which has a hand-held main body, wherein a plasma source is arranged on the main body and is designed for generating a non-thermal plasma. The plasma device also has a spacer which is configured when assembled to define a distance between the plasma source and a body treatment surface. The spacer is detachably connectable, and preferably connected, to the main body and/or to the plasma source. By means of the spacer, it is possible to easily and precisely maintain a predetermined distance defined by the spacer between the plasma source and the treated body surface, in particular by placing the end of the spacer which faces away from the plasma source on the body surface. Since the spacer can be detachably connected to the main body and/or the plasma source, it is possible to exchange it easily. This in turn makes it possible to use different spacers, and therefore in particular also different spacings, for different treatments, wherein the spacer and the corresponding spacing can be selected to match the intended treatment. A spacer can be easily and effortlessly exchanged for another spacer. At the same time, the detachable attachment of the spacer to the main body and/or the plasma source enables the spacer to be cleaned, in particular sterilized or disinfected, or even disposed of after use—separately from the rest of the plasma device. The spacer is particularly preferably designed as a disposable part for one-time use, that is to say as a disposable article.

Particularly preferably, the spacer can be delivered in sterile packaging, removed from the sterile packaging immediately before its use, and connected to the main body and/or the plasma source; after this, it is used together with the plasma source; and after completion of a plasma treatment, it is detached from the main body and the plasma source and is disposed of in a suitable manner—in particular as contaminated waste.

According to the invention, the plasma source is detachably connected to the main body. This enables the plasma source, which may possibly be contaminated by the plasma treatment of a body surface, to be cleaned in a simple manner. The plasma source can then be removed from the main body and cleaned, disinfected and/or sterilized independently of the main body—in particular in an ultrasound bath. It is advantageous in this case that the plasma source itself does not have to have any electronic components, and can therefore also be disinfected or sterilized under certain conditions which could not be utilized without damage to the main body, which preferably comprises electronic components such as a control device, an electrical storage device, in particular an accumulator or a battery or the like. In particular, the plasma source can have a completely encapsulated structure, solely with contacts which are routed to the outside for the purpose of contact with a control device, such that it can be directly exposed to more aggressive cleaning, sterilization or disinfection methods—whether by treatment with chemicals, steam, ultrasound and/or autoclaving.

In addition, the detachable connection of the plasma source to the main body enables the plasma source to be exchanged in a simple manner if it should be damaged, without the main body having to be disposed of as a result. Conversely, however, the main body can also be exchanged if there is a defect in it, in which case the plasma source can then continue to be used with another main body.

The detachable spacer, on the one hand, and the detachable plasma source, on the other hand, make it possible, in particular in combination with each other, for the parts of the plasma device which come in touching contact with a treated surface or can otherwise become non-sterile to at least be cleaned and sterilized or disinfected prior to further use—especially for another patient—which is preferably particularly relevant for the plasma source, or to be designed as disposable parts and only used once, which is particularly relevant for the spacer. In combination with each other, the detachable spacer and the detachable plasma source accordingly offer the possibility of operating the plasma device in a simple and economical manner, particularly hygienically and safely.

It is provided in particular that the spacer and the plasma source can be separated from each other so that, for example, the spacer can be disposed of while the plasma source can be cleaned, disinfected and/or sterilized and then reused. Overall, the plasma device thus comprises at least three parts, namely the main body, the plasma source and the spacer, which on the one hand can be separated from each other, while the plasma device on the other hand can be put together by connecting the plasma source to the main body and by connecting the spacer to the plasma source and/or the main body.

The fact that the plasma device is designed to be held in the hand means in particular that it can be carried by a user and held—in particular in one hand—during a treatment. The size of the plasma device corresponds in particular to a telephone receiver, a shower head or the like, and consequently an object that can be held and operated easily and effortlessly with just one hand.

The plasma device is preferably designed as a stand-alone device that can be operated independently of other devices, in which case it is in particular wireless in design, preferably battery or accumulator-operated, such that it is not permanently connected to another device or another apparatus.

However, the plasma device is preferably assigned a charging station in which the main body can be arranged in order to store the plasma device, on the one hand, and to charge an electrical storage device, in particular an accumulator or battery which is preferably integrated in the main body, on the other hand.

Since the plasma source is configured in particular for generating a plasma in ambient air, there is no need for a special gas feed to the plasma source, such that the main body can also be moved and operated independently of any other devices.

A non-thermal plasma is understood to mean, in particular, a plasma in which a temperature describing the distribution of the kinetic energy of the electrons in the plasma, which is also referred to as the electron temperature, is not identical and in particular is much higher than the distribution of the kinetic energy of the ions contained in the plasma—in particular, the temperature describing atomic ions or molecular ions, which is also referred to as the ion temperature. The electron temperature is very much higher than the ion temperature, wherein the ion temperature is preferably selected to be in the range from 25° C. to at most 100° C. Such a plasma is also referred to as a cold plasma due to the comparatively low ion temperature.

A state of matter in which charged particles with positive and negative charges are present next to each other in a gas phase, with a neutral electrical charge averaged over a certain volume resulting for the volume under consideration, is referred to here as a plasma. The plasma also preferably comprises uncharged atoms and/or molecules which are in electronically, vibratory and/or rotationally excited states, and which are also referred to as excited particles, and/or free radicals—and therefore overall, in particular uncharged reactive atoms and/or molecules, also known as reactive particles or reactive species.

The spacer preferably has a circumferential—in particular circumferentially closed—edge which, when the plasma device is used to treat a body surface, encloses a volume to be treated, with the body surface and the plasma source together—in particular in a fluid-tight manner or with a remaining air gap. In this way, on the one hand, a plasma chemistry can take place inside the closed or almost-closed volume, unaffected by environmental influences, in particular unaffected by drafts; on the other hand, a user of the plasma device and a patient on whom the plasma device is used are protected from toxic substances that arise in the closed volume, possibly and particularly by inhalation. In particular, inhalation of ozone is prevented.

According to a further development of the invention, it is provided that the spacer has a circumferential collar which, when installed, overlaps the plasma source and partially overlaps the main body. As a result, the spacer is held in a stable manner on the main body and the plasma source. If the main body and the plasma source have a non-circular geometry, at least in the area in which they are encompassed by the circumferential collar, the collar, which is preferably complementary to the geometry of the plasma source and the main body and sits snugly on the same, secures the spacer against accidental rotation relative to the plasma source and the main body. The plasma source is itself detachably arranged on the main body. The circumferential collar of the spacer, which, when installed, simultaneously overlaps the plasma source and partially overlaps the main body, furthermore also secures the plasma source against accidental detachment from the main body.

The spacer has in particular—starting from a central region along an imaginary axis which is perpendicular, when in the treatment position, to the treated body surface—in a first direction the circumferential edge, which extends in particular in the distal direction, i.e. towards the body treatment surface, and, in a second direction, the circumferential collar which, starting from the central region, extends in the proximal direction, that is to say towards the plasma source and the main body and away from the body treatment surface. The fact that the edge and the collar are designed to be circumferential means in particular that they surround the imaginary axis along a closed line.

According to a development of the invention, it is provided that the spacer has at least one first snap-on element and the plasma source and/or the main body has/have at least one second snap-on element, wherein the first snap-on element and the second snap-on element are complementary to each other in such a manner that the first snap-on element and the second snap-on element can work together to hold the spacer on the main body and/or the plasma source. In this way, the spacer can be snapped onto the main body and/or the plasma source in a simple and detachable manner, such that it is held securely and stably on the main body and the plasma source, in particular during a treatment. It is possible for the spacer—and accordingly the main body and/or the plasma source—to have more than one first snap-on element, and accordingly also more than one second snap-on element assigned thereto. In particular, it is possible for the spacer to have a first snap-on element on each of two sides opposite each other perpendicular to the imaginary axis, wherein the main body and/or the plasma source accordingly have two second snap-on elements arranged on two opposite sides, as seen perpendicular to the imaginary axis. The first snap-on elements can then interact with the second snap-on elements assigned to them in order to hold the spacer on the main body and/or the plasma source.

The at least one first locking element is preferably designed as a projection, in particular in the form of an undercut, or as a recess, wherein the second locking element is designed in a complementary manner as a recess or projection, in particular an undercut, wherein the locking elements made in the manner of a projection which engages in a recess can cooperate in order to snap the spacer onto the main body and/or the plasma source. Particularly preferably, a projection or an undercut is formed on the spacer as a first snap-on element, wherein a recess is formed as a second snap-on element on the plasma source or the main body, particularly preferably on the plasma source. However, the reverse configuration is also possible.

According to a development of the invention, it is provided that the spacer has a tab extending from the circumferential edge or from the circumferential collar, which when installed extends in the direction of the main body and is designed for detaching—in particular, manually—the spacer from the main body and/or the plasma source. The tab extends in particular in the proximal direction as seen along the imaginary axis. It is designed so that it can be grasped from behind in order to release the spacer from the plasma source and/or the main body—in particular by a finger or thumb—wherein the spacer can be pushed off of the main body and/or the plasma source in a simple manner by pushing the tab from behind—in particular with only one hand. Particularly preferably, the tab is oriented and/or aligned in such a way that the operator's hand which is holding the main body can push it from behind, in particular with the thumb or another finger, wherein the spacer can then be detached from the plasma source and the main body with one finger, for example the thumb or another finger, and disposed of. This enables a particularly hygienic, and at the same time simple, removal of the spacer, which can be transported into a disposal container without touching the operator's other hand—and most importantly, with a simple finger movement of the operating hand.

According to a development of the invention, it is provided that the spacer has an electronic identification device. The electronic identification device can be configured in a particularly simple embodiment in order to simply ensure that the spacer is only used once. This can—which will be explained in more detail below—be achieved by unambiguous identification of the spacer; however, it is also possible for the identification device to have at least one switchable bit which, in a first switching state, indicates that the spacer has not yet been used, and the switchable bit, in a second switching state which is different from the first switching state, indicates that the spacer has already been used once. The plasma device, in particular a control device of the plasma device, is then preferably configured to switch the at least one switchable bit of the electronic identification device from the first switching state to the second switching state before, during or after the use of the spacer. The switchable bit is preferably queried before the plasma device is used, wherein the use of the plasma device is preferably only enabled when the switchable bit is arranged in the first switching state—i.e., it indicates that the spacer has not yet been used.

It is possible for a predetermined downtime to be provided. A period of time since the end of a use of the plasma device is captured and compared with the predetermined downtime. If the captured time until the plasma device is next used exceeds the predetermined downtime, further use with the same spacer is blocked—that is, the plasma device can only be used again after the spacer has been changed. Re-use of the plasma device with the same spacer is only possible within the predetermined downtime. The detection of the duration preferably starts anew with each termination of an individual use of the plasma device. This makes it possible in particular to carry out successive uses—which follow each other before the end of the predetermined downtime—with one and the same spacer, which in turn makes it possible, for example, to treat larger areas of a treatment surface successively with the plasma device, without changing the spacer. Typically, the change to another patient and/or another, non-contiguous location on a treatment surface, for example to another wound on the body of a patient, requires a longer period of time than the simple successive treatment of a contiguous surface area—in particular, the same wound, for which there is no need to replace the spacer.

According to a more complex embodiment, the electronic identification device can, in addition or as an alternative to the at least one switchable bit, enable a particularly unambiguous identification of the spacer—for example by means of an alphanumeric code or the like. Preferably, additionally or alternatively, the distance which the spacer defines between the plasma source and the treatment surface is also stored in the electronic identification device. In this way, the spacer can be identified easily and in particular automatically, wherein it is possible, on the one hand, to ensure that the correct spacer is used with the correct, required spacing for the selected type of treatment, and/or wherein, on the other hand, it can be ensured that the spacer is used only once, or multiple times only on one treatment point, or only a predetermined number of times. This leads to increased safety in the use of the plasma device, wherein the operator himself is supported in selecting the correct spacer and is prevented from accidentally using the spacer multiple times. The operator can then concentrate fully on the actual treatment.

At least one parameter for the plasma generation, that is to say in particular for the operation of the plasma device, is preferably stored in the electronic identification device. This at least one parameter is preferably characteristic of the use for which the spacer having the electronic identification device is intended, and/or it is specifically matched to the design of the respective spacer. In particular, a treatment duration for the treatment of a surface with the plasma device having the spacer can be stored as such a parameter, wherein the treatment duration depends in particular on the volume which is enclosed by the spacer, and in particular its circumferential edge.

The plasma device, in particular the control device of the plasma device, is preferably configured to only activate the plasma source, i.e. to only start plasma generation, when the presence of a spacer on the plasma source and/or the main body is determined—in particular by means of the electronic identification device. In addition, if no spacer can be identified, the plasma generation is preferably blocked—that is, the plasma source can preferably not be activated or operated without arranging a spacer on it and/or the main body.

Data, parameters or the like stored on the electronic identification device—in particular, also the at least one switchable bit described above for determining a previous use of the spacer—are preferably stored in encrypted form in the electronic identification device. The control device of the plasma device preferably has a decryption device which is configured to decrypt the encrypted data read from the electronic identification device. The spacer can therefore only be used with a plasma device which is able to decrypt the data stored on the electronic identification device. Conversely, if the control device of the plasma device is not able to decrypt data downloaded or read from a spacer, or the electronic identification device of the spacer, it recognizes a missing spacer, such that operation of the plasma source is preferably blocked.

The electronic identification device can preferably be read in a contactless manner, such that there is no need for the main body and/or the plasma source to contact the spacer. In particular, the electronic identification device is preferably designed as an RFID label (RFID tag), which is a simple and inexpensive way of producing an electronic identification device.

According to a development of the invention, the electronic identification device is preferably integrated into the tab, which results in an arrangement of the electronic identification device that is both space-saving and favorable for contactless reading.

Alternatively or additionally, it is preferably provided that a primary plane of the electronic identification device is perpendicular to an electrode surface of the plasma source. This approach prevents electromagnetic fields generated by the plasma source during operation from interfering with the contactless reading of the electronic identification device, because the fields used for reading are accordingly oriented perpendicular to the fields generated by the plasma source. A primary plane of the electronic identification device is understood to mean, in particular, a plane in which an inductive part of an oscillating circuit of the electronic identification device is arranged—in particular, a plane in which a spirally wound coil part of an RFID label is arranged. The electrode surface of the plasma source is in particular a plasma generating surface, that is to say a surface on which the non-thermal plasma—in particular in the form of surface micro-discharges—is generated.

According to a further development of the invention, it is provided that the plasma device—as already mentioned multiple times—has a control device which is configured to read and/or write to the electronic identification device of the spacer, preferably to identify the spacer, and preferably to only allow a single use of the spacer—or multiple uses only in one location. This make it possible particularly to ensure that each spacer is used only once, or at most multiple times in one location.

For this purpose, the at least one switchable bit is preferably used on the electronic identification device, which—as already described—is preferably switched by the control device before, during or after use of the spacer during a plasma treatment. In this way, the information as to whether the spacer has already been used can be stored on the spacer itself, in particular on the electronic identification device.

However, it is also possible that the control device can in particular store the identification data of the already-used spacers at least for a certain time, and in each case can compare the identification data of a spacer, at the time it is read, with the stored identification data. In practice, it will not be necessary to keep the identification data of the used spacers for a long time, since it is unlikely that a spacer that has already been used will be used again after several days, weeks, months or even years. In contrast, an oversight that occurs more frequently is likely to result from the fact that the spacer is inadvertently not released after being used on a patient, and is then used again on another patient. In any case, instructions to a user of the plasma device should provide for the spacer to be disposed of immediately after it has been used once, or optionally multiple times in the same location. It could therefore theoretically suffice if the control device only stores the identification data of the most recently used spacer. However, safety can be increased if a larger number of identification data of the most recently used spacers is stored. For example, a ring memory can be used, in which the oldest identification data is always deleted when new identification data is stored. However, it is also possible for identification data to be deleted from the memory after a predetermined time has elapsed. However, if a sufficiently large memory is available for the control device, there may be no need to delete identification data at all over the life of the plasma device.

The control device is therefore preferably configured to compare the currently read identification data of a spacer with the stored identification data and to refuse to use the currently installed spacer if its identification data matches any of the stored identification data. If this is the case, an alarm or an error message can be output, for example, in particular in the form of a light signal, an acoustic signal, and/or a text notification if the plasma device has a display. Alternatively or additionally, the control device can block the operation of the plasma device until a new spacer has been installed.

The predetermined downtime already described above can also be used with a view to evaluating the identification data to enable the use of a spacer, in particular to allow the spacer to be used in the same location multiple times. A use in the same location multiple times is understood to mean that the plasma device is applied and activated multiple times in order to cover an area, i.e. in particular a surface area, for example, to treat a wound, wherein the area has a greater planar extension than the spacer or the plasma source, such that multiple applications are necessary to treat the entire area. The current identification data is therefore preferably stored—as it were, in the blacklist of the identification data—only after the predetermined downtime has elapsed.

The control device is preferably integrated into the main body. It is particularly preferably operatively connected to the plasma source in order to operate it. The control device therefore also serves in particular to activate, in particular to energize, the plasma source. The control device can itself have a high-voltage source, or can be designed as a high-voltage source. The control device can, however, also be operatively connected to a high-voltage source in order to activate it to energize the plasma source.

According to a further development of the invention, it is provided that the spacer has a blocking element which is permeable to non-thermal plasma, but at the same time, when in the installed state, is designed to prevent the treated body surface from contacting the plasma source. The blocking element is preferably arranged in the spacer on the inside thereof, in particular in the central region, which is preferably arranged between the circumferential edge and the circumferential collar. According to a preferred embodiment, the blocking element is designed as a grid. The blocking element increases the electrical safety during handling of the plasma device. In particular, it prevents accidental contact and thus also contamination or soiling of the plasma source while it is in operation.

In this respect, it is preferred that the control device only enables operation of the plasma source when a—not yet used—spacer is actually arranged on the plasma source and/or the main body, this being preferably recognized by means of the electronic identification device.

The plasma source can preferably be connected to the main body via a connecting device, the connecting device having a plug-and-turn mechanism, preferably in the manner of a bayonet lock. This enables the plasma source to be attached to the main body in a simple and secure manner.

As an alternative or in addition, the connecting device is designed asymmetrically in such a way that the plasma source can only be attached to the main body in a specific orientation. The term "orientation" here refers in particular to a certain rotational or angular position around the imaginary axis, which is also preferably the plug-in axis of the connecting device designed as a plug-and-turn mechanism, wherein the imaginary axis then preferably also forms the axis of rotation of the plug-and-turn mechanism. The plug-and-turn mechanism is preferably designed in such a way that the plasma source is first plugged onto the main body, when viewed along the imaginary axis and when in an unlocking position, and then the plasma source is rotated about the imaginary axis into a locking position. The asymmetrically configured connecting device advantageously enables the plasma source to always be attached to the main body in the correct orientation, which in particular enables an unambiguous and reliable contact to be made with the plasma source.

In particular, the plasma source preferably has two electrodes; of these, the same electrode should always be connected to high voltage, and the other should be connected to ground. Faulty electrode contacting can be avoided by means of the asymmetrical connecting device, such that the electrode which must be grounded is not accidentally subjected to high voltage. This further increases the electrical safety of the plasma device.

The connecting device is preferably configured asymmetrically by the fact that it has asymmetrical connecting means. For example, it is possible for the plug-and-turn mechanism to have asymmetrically designed plug-in receptacles and asymmetrically designed plug-in elements, so that the plasma source can only be plugged in in a predetermined position. Alternatively or additionally, at least one asymmetrically and/or eccentrically—that is, radially spaced from the imaginary axis—arranged projection, in particular in the form of a snap hook, is provided on the plasma source and/or the main body, wherein the other element, selected from among the main body and the plasma source, has a corresponding eccentrically arranged and/or asymmetrical recess. A connection between the plasma source and the main body can then preferably only be closed when the eccentrically arranged projection engages in the eccentrically arranged recess and/or when the asymmetrically formed projection engages in the corresponding, asymmetrically formed recess. In the wrong angular position, on the other hand, the projection and the recess are preferably not in overlap with each other, or at least not in an overlap that allows the projection to be introduced into the recess, such that a distance or gap remains between the plasma source and the main body which does not allow a firm connection between the plasma source and the main body.

At least one such asymmetrical and/or eccentrically arranged projection, in combination with a corresponding recess, can also—in addition or as an alternative to the orientation function explained above—serve to pretension the plasma source on the main body so that it is held securely and stably. For this purpose, the at least one projection is preferably designed to be elastic, such that it is configured to apply an elastic pretension in particular along the imaginary axis. The corresponding recess is then preferably designed in such a way that it compels the elastic projection into an elastically pretensioned functional position, at least in the assembled position of the plasma source. The recess can in particular be designed as a circular arc-shaped groove with—as seen in the circumferential direction—varying depth, such that the elastic projection can preferably initially engage unloaded into the groove when the plasma source is plugged onto the main body, wherein it is compelled into a preloaded position by the bottom of the groove, the depth of which decreases in this direction, during the rotational movement of the plasma source into its assembled position.

Conversely, however, it is also possible for the elastic projection to produce a pretension when it is set in place, wherein it is at least partially relieved when the plasma source is installed. In this embodiment, the feedback perception for a user of the plasma device when assembling the plasma source is improved.

According to a development of the invention, it is provided that the plasma source is configured for generating surface micro-discharges (SMD) in ambient air on a discharge surface of the plasma source. This discharge surface is a plasma generation surface of the plasma source, on which the plasma is generated. It has been found that a plasma source configured in this way is particularly suitable for treating body surfaces. In particular, a plasma can be generated without the body surface itself having to be utilized or included in the circuit as an electrode.

The plasma source preferably has a first, planar electrode and a second, planar electrode, and also a dielectric, by means of which the first electrode and the second electrode are spaced from each other. Both electrodes are in direct mechanical contact with the dielectric; they are preferably in close contact with the dielectric or are embedded in the dielectric. In any case, the first electrode is arranged on a first side of the dielectric, and the second electrode is arranged on a second side of the dielectric, and furthermore the stack arrangement of the electrodes and the dielectric is formed on the same side of the treated body surface. The body surface is therefore in particular not arranged between the dielectric and one of the electrodes, on one side, and the other electrode, on the other side; rather all electrodes and the dielectric are arranged on the same side of the body surface. The body surface is also not used as an electrode or counter electrode; in particular, it is not electrically contacted.

A potential difference—in particular in the form of an alternating voltage—can be applied to the electrodes for generating the non-thermal plasma on the discharge surface assigned to one of the electrodes.

The first electrode is preferably designed with a solid surface, wherein the second electrode is designed in a structured manner, having a large number of edges at which the surface micro-discharges ultimately occur. The second electrode can in particular be designed as a grid or in another suitable manner. A high voltage is preferably applied to the first electrode, the second electrode being connected to ground, or grounded. The second electrode is preferably arranged distally, that is to say facing the body treatment surface, wherein the first electrode is arranged proximally, that is to say facing away from the body treatment surface. As a result, the grounded electrode at which the plasma is generated faces the body surface, which additionally increases the electrical safety of the plasma device. In particular, the first high-voltage electrode can be arranged encapsulated within the plasma source.

According to a development of the invention, it is provided that the first electrode and the dielectric and/or the second electrode and the dielectric are pressed against each other by a biasing element or pressing element. It is thus possible to provide the electrode arrangement consisting of the first electrode, the dielectric and the second electrode inexpensively and, at the same time, with optimal plasma generation, with no air gap—or at most a small air gap between the electrodes and the dielectric, due to the manufacturing process. The electrode arrangement is preferably at the same time compelled by the biasing element or pressing element against a wall of the plasma source, in particular against a wall of a housing of the plasma source in which the electrode arrangement is arranged.

It is possible for both electrodes to be placed loosely on the dielectric, wherein they are pressed against the dielectric by the biasing element or pressing element. However, it is also possible for the first electrode to be coated onto or glued to the dielectric, wherein only the second electrode is designed to be loose and is compelled against the dielectric by the biasing forces of the biasing element or pressing forces of the pressing element.

Alternatively, however, it is also possible for both electrodes to be coated onto or glued to the dielectric.

It is also possible for at least one electrode selected from the first electrode and the second electrode to be embedded in the dielectric, and it is also possible for both electrodes to be embedded in the dielectric, on opposite sides.

A stacking direction of the stack from the first electrode, the dielectric and the second electrode extends in particular along the imaginary axis.

The electrode arrangement is pushed against the wall of the housing, in particular at least in regions, in particular in an edge region, by the biasing element or pressing element, wherein the corresponding housing wall has a central recess for the passage of plasma. The second electrode is preferably exposed through this recess, such that the plasma generated at the second electrode can pass through the corresponding wall of the plasma source.

According to a further development of the invention, it is provided that the electrode arrangement and preferably the biasing element or pressing element are arranged in the housing of the plasma source, and are preferably sealed in the housing. This enables the electrode arrangement to be encapsulated in a particularly favorable manner, wherein the plasma source as a whole can be cleaned, preferably sterilized or disinfected, in a simple manner. In particular, the plasma source as a whole can be placed in an ultrasound bath in order to clean or disinfect it. While the housing preferably has the wall, which has the central recess for the plasma passage, on its distal side, it is preferably closed by a cover element on its proximal side, i.e. on its rear side, the cover element preferably being screwed or connected in other ways to the housing. The cover element preferably comprises the connecting device which is provided for connecting the plasma source to the main body.

According to a further development of the invention, it is provided that the plasma device has a safety circuit which is configured to de-energize and/or cut the current to an electrical contact when the plasma source is detached from the main body, said electrical contact being configured for the electrical connection of the plasma source to a high-voltage source arranged in the main body, and to allow voltage and/or current to flow to the electrical contact only when the plasma source is arranged on the main body. This considerably increases the electrical safety of the plasma device for a user. In particular, the risk of electric shock when the plasma source is separated from the main body is significantly reduced, preferably eliminated.

For this purpose, the safety circuit has a break in an electrical supply line from an electrical storage device—in particular, the accumulator or the battery—to the high-voltage source, preferably on an end face of the main body, wherein the plasma source has a bridging contact facing the end face when in the installed state on the main body, which is configured and arranged to electrically bypass the break when the plasma source is arranged on the main body. If, on the other hand, the plasma source is separated from the main body, the electrical supply line to the high-voltage source is broken so that it is not supplied with electrical power. In this case, the electrical contact for the plasma source is therefore without current and/or voltage.

The break preferably has two safety contact pins on the end face which are electrically isolated from each other and spatially distanced from each other. The bridging contact is preferably configured to electrically connect the safety contact pins to each other when the plasma source is arranged on the main body. The bridging contact is preferably designed as a contact plate or the like.

According to a further development of the invention, it is provided that a control device of the plasma device is configured to carry out a functional verification of the electrode arrangement, with the following steps: determining at least one power parameter characterizing a plasma power of the electrode arrangement; comparing the at least one power parameter with at least one predetermined target parameter value; obtaining a comparison result; and assessing a functionality of the electrode arrangement on the basis of the comparison result. The power parameter is determined in particular when the electrode arrangement is in operation; it is particularly characteristic of a momentary plasma power of the electrode arrangement during its operation.

By means of this functional verification, it is possible, particularly at first when the electrode arrangement is put into operation, and in particular before it is used, to reliably and precisely determine its functionality, and thus in particular to prevent the dangers associated with poor, reduced or failed functionality of the electrode arrangement for a user of the plasma device, or for third parties.

At least one action is preferably selected as a function of the comparison result. In this way it is possible to react to the comparison result and thus also to the ascertained functionality of the electrode arrangement, and to select an action adapted to this.

A plasma power of the electrode arrangement is understood to mean the portion of the electrical power consumed by the electrode arrangement which is used directly for generating the non-thermal plasma, and which is in particular directly related to a generation rate for reactive particles comprised by the plasma. If a parameter is captured as the power parameter that is characteristic of this plasma power, conclusions can be drawn in a particularly safe and reliable way about the functionality of the electrode arrangement, because the power parameter in this case provides direct information about the plasma generation by the electrode arrangement.

An assessment of the functionality of the electrode arrangement is understood to mean, in particular, that a statement about the functionality of the electrode arrangement is derived, either indirectly by selecting a certain action and/or directly by outputting a message describing or identifying the functionality of the electrode arrangement. The functionality can be assessed in this case as a simple, binary determination, namely whether the electrode arrangement is functional or not. However, it is also possible for the functionality of the electrode arrangement to be assessed in a more complex way, in particular with regard to determining the momentary plasma power and possibly the selection of an action depending on the determined momentary plasma power.

In the context of the functional verification, the plasma power is preferably captured as a power parameter or with respect to the at least one power parameter.

According to a further development of the invention, it is provided that the action is selected from a group consisting of an output of an "OK" signal, an output of a "action needed" signal, an output of a "Not OK" signal, a notification to an operator of the electrode arrangement of the—in particular, momentary—plasma power, an adaptation of an operating period or treatment duration to the comparison result, termination of the operation of the electrode arrangement, and continuation of the operation of the electrode arrangement without further measures, in particular without outputting a signal or a message. An "OK" signal is also referred to as a green signal, an "action needed" signal is also referred to below as a yellow alarm, and a "Not OK" signal is also referred to below as a red alarm. A green signal indicates that the electrode arrangement is working as intended.

The green signal can in particular be output if the at least one power parameter deviates from the predetermined target parameter value by less than a first predetermined limit value, for example by less than 15%. A yellow alarm informs an operator of the electrode arrangement that the electrode arrangement should be checked, wherein further steps may optionally be necessary, for example cleaning the electrode arrangement, cleaning contacts, or other such measures. Such a yellow alarm is preferably output when the deviation of the at least one power parameter from the at least one predetermined target parameter value is greater than the first predetermined limit value, and is less than a second predetermined limit value, wherein the second predetermined limit value is greater than the first predetermined limit. The second predetermined limit value can correspond, for example, to a deviation of 30% from the predetermined target parameter value. The yellow alarm can also be output if the deviation of the at least one power parameter from the at least one predetermined target parameter value is equal to the first predetermined limit value. A red alarm can in particular be output if further operation of the electrode arrangement is no longer useful due to insufficient functionality, or is dangerous either for the electrode arrangement itself, for the operator, or for a person treated with the electrode arrangement. The red alarm can in particular be output if the at least one power parameter deviates from the at least one predetermined target parameter value by the second predetermined limit value or by more than the second predetermined limit value.

According to one embodiment of the functional verification, the at least one predetermined target parameter value can be a target value, in which case the power parameter is compared with the—in particular, exactly one—target value, and the functionality of the electrode arrangement is assessed on the basis of the comparison result. In particular, a deviation from the target value both upwards and downwards, at least when certain limit values defined relative to the target value are exceeded, is an indication of a deficient functionality of the electrode arrangement.

According to another embodiment of the functional verification, it is possible for the at least one predetermined target parameter value to be a minimum value. In this case, the power parameter is compared with the minimum value in such a way as to provide a verification of whether the power parameter is greater or less than the minimum value. The electrode arrangement is functional when the power parameter is greater than or equal to the minimum value, and the electrode arrangement is not functional if the power parameter is less than the minimum value. A range for a yellow alarm can also be defined, wherein this then extends, starting from the minimum value, up to a predetermined limit value which is less than the minimum value by a predetermined amount or a predetermined factor. The range for the red alarm then extends, starting from the predetermined limit value, towards lesser values, wherein the range for the yellow alarm is found between the predetermined limit value and the minimum value. In this case, the range for the green signal is above the minimum value.

In a corresponding—but simply opposite—way, in a further embodiment of the functional verification, the target parameter value can be defined as the maximum value. The electrode arrangement is not functional if the power parameter assumes values above the maximum value, wherein the electrode arrangement is functional when the power parameter assumes values below or up to the maximum value. The range of the green signal then extends from smaller values, in particular from zero, up to the maximum value, wherein the range of the yellow alarm extends, starting from the maximum value, to a predetermined limit value, which is greater than the predetermined limit value by a predetermined amount or a predetermined factor. The range of the red alarm then extends from the predetermined limit value to higher values.

In a further embodiment of the functional verification, it is possible that two predetermined target parameter values are provided, and the at least one power parameter is compared to these. The two predetermined target parameter values define a value band or limits of a value range, wherein the electrode arrangement is assessed as being functional within this value band or value range. In particular, a first predetermined target parameter value is defined as the minimum value of the value band or value range, with a second, greater target parameter value being defined as the maximum value of the value band or value range. The ranges for the yellow alarm are then each assigned to the maximum value on the one hand and the minimum value on the other hand, in the same way as was explained above for the minimum value and the maximum value.

Alternatively, it is also possible that a range for a yellow alarm does not—as explained above—extend in the direction of the range for the red alarm, starting from the predetermined target parameter value, but rather that it extends into the range of the green signal. In this case, for example, the predetermined limit value assigned to the minimum value can be greater than the minimum value, wherein the predetermined limit value assigned to the maximum value can be less than the maximum value. Alternatively, it is also possible to define a yellow alarm area in such a way that it includes, preferably symmetrically, the predetermined target parameter value.

The at least one predetermined target parameter value is preferably selected as a function of a desired operating mode of the electrode arrangement, in particular as a function of a desired plasma chemistry, especially a desired concentration of certain active species in the plasma. For example, it is possible that different target parameter values, in particular a permissible value range or a permissible value band, are specified on the one hand for the case that the generated non-thermal plasma needs to substantially contain oxygen species, for example ozone (oxygen mode), or the case that the non-thermal plasma should substantially contain nitrogen species, in particular nitrogen oxides (nitrogen mode). It is also possible to choose an intermediate range between these operating modes. The plasma chemistry depends heavily on the selected plasma power, and can therefore be specified by this. In this respect, the functionality of the electrode arrangement must also be tested with respect to the plasma power according to the selected operating mode.

The signals described here can be output as light signals, for example. In particular, it is possible for the green signal to be output as a green glowing light, the yellow alarm as a yellow glowing light, and the red alarm as a red glowing light. In particular, light-emitting diodes can be used to output the light signals.

The signals and/or messages can, however, alternatively or additionally also be output in text form, in particular in a display, as acoustic signals or messages, by vibration, or in another suitable manner.

A communication of the particular momentary plasma power to the operator enables the operator to estimate a treatment outcome of the electrode arrangement for a specific treatment duration and, if necessary, to adapt the treatment duration to the momentary plasma power. If, for example, the electrode arrangement has an momentary plasma power that is reduced compared to a nominal plasma power, the operator can extend the duration of treatment in a suitable manner in order to apply a specific plasma dose. Such an adaptation of the treatment duration can, however, preferably also take place automatically, in particular as a function of the comparison result. The operator is preferably informed about the automatically modified duration of treatment, or the operator is required to operate the electrode arrangement until its automatic termination of operation, in which case the modified treatment duration is taken into account essentially automatically. In this case, the treatment duration preferably corresponds to an operating duration of the electrode arrangement, since it is preferably only operated during a treatment that is actually carried out. Treatment then begins, in particular, with the beginning of operation of the electrode arrangement, and ends with the termination of operation of the electrode arrangement.

If an undiminished functionality of the electrode arrangement is determined, its operation is preferably continued. In particular, the operation of the electrode arrangement can be continued at the same time as the output of a green signal, in particular if the functional verification is carried out when the electrode arrangement is put into operation. If the functional verification is carried out while the electrode arrangement is in operation, operation is preferably continued when an undiminished functionality is determined, without further measures being carried out, in particular without outputting signals.

According to a development of the invention, it is provided that the functional verification is carried out immediately after the electrode arrangement has been put into operation. In particular, it is possible for the functional verification to be carried out—in each case, anew—immediately after the electrode arrangement has been put into operation. In this way, the electrode arrangement can be checked directly at the time it is put into operation, with the operator of the electrode arrangement preferably being given feedback as to whether the electrode arrangement is functional. In this way, before the actual use of the electrode arrangement, in particular before treating a surface or person with the electrode arrangement, it can always be determined whether the electrode arrangement is functional, wherein optionally the actual use of the electrode arrangement does not take place, and the same is checked, cleaned or sent to repair instead. On the one hand, this has the advantage that the operator is informed without delay about problems with the electrode arrangement, thereby preventing inadequate treatment or, possibly, a treatment which is not performed, without this being recognized, wherein measures can be taken directly to maintain or ensure the functionality of the electrode arrangement. Knowing whether the electrode arrangement is functional immediately at the moment when it is put into operation is also advantageous for any treatment protocols which must be arranged.

The functional verification can be initialized in an event-driven manner, for example by an external request, in particular by a manual request by an operator. The functional verification is particularly preferably started automatically.

In particular, the plasma power can be determined in various ways:

A preferred option is Fourier (or power spectrum) analysis, where only the power in the high-frequency part of the spectrum is determined. Since the plasma discharges generate many small "spikes" (essentially like delta functions), the plasma power can be measured in the high frequency range.

In another preferred measurement method, the plasma power is described by the area of a Lissajous figure which is generated by a phase space diagram of a control voltage, which is defined as the voltage that is applied to the electrode arrangement for plasma generation by means of a high-voltage source, plotted against a plasma voltage, which is defined as the voltage that is actually applied across the electrode arrangement during its operation, wherein the control voltage is accordingly the unmodified operating voltage of the plasma device and the plasma voltage is the voltage which is modified/deformed by plasma discharges, phase-shifted relative to the control voltage, and which drops across the electrode arrangement. In this case, it is preferred to not take into account the individual micro-discharges in the voltage curve, but rather a suitable averaging.

The phase space diagram creates a closed curve around an enclosed area. This enclosed area contains information about the deformation of the control voltage caused by the micro-discharges, as well as the phase shift between the control voltage and the plasma voltage, and thus constitutes a measure of the plasma power.

In practice, for various reasons, it is not always possible to use this phase space diagram and/or to measure the voltage curves directly. Control voltage then means: applied high voltage or voltage which corresponds to the applied high voltage in form, phase and amplitude; and instead of the plasma voltage, a proxy voltage is measured, which drops across an electronic proxy structure connected in series with the electrode arrangement—in particular also referred to as "proxy measurement"—wherein the proxy voltage is generated by effects (deformation and phase shift) caused by the micro-discharges (which contain the actual plasma power). The enclosed area of this "proxy measurement" or the proxy voltage in itself also describes the plasma output.

There are various ways to carry out such a "proxy measurement" which represents the plasma power:

1. The phase space curve of the control voltage is plotted against the proxy voltage, and the integral of the area enclosed in this way is taken.
2. The proxy voltage is measured at a specified point in time in the sine curve of the control voltage. The positioning of this point in time of the control voltage is optimally chosen such that the maximum width and/or height of the Lissajous figure is targeted. This position is optimally in the area of the greatest temporal gradient and/or phase difference between the control voltage and the proxy voltage.

An easily definable point for this measurement is the zero crossing of the control voltage. The proxy voltage at this point is close to the maximum width or height of the Lissajous figure. The proxy voltage detected in this way is an easily measurable parameter that represents the plasma power. For this purpose, a suitable choice of a proportionality factor is required; this can be determined in particular by comparison with the enclosed area of the Lissajous figure.

Because of the "discretization" of the measurement, a micro-discharge may or may not be found by chance with such a singular measurement. For this reason, a sufficient number of measurements—preferably 256 measurements—is preferably averaged in order to obtain a reliable result for the plasma power.

According to a further development of the invention, it is provided that the at least one power parameter is detected in an electronic proxy structure connected in series with the electrode arrangement, in particular an electronic proxy structure of the plasma device, in particular as a proxy measurement. This enables a simple measurement of the power parameter, which can be carried out in particular even with a small, portable, hand-held device, and which is nevertheless characteristic of the plasma power of the electrode arrangement.

An electronic proxy structure is understood here to mean in particular an electronic component or a plurality of electronic components electrically connected directly or indirectly and interacting with each other, which is particularly suitable for allowing the performance of a proxy measurement to determine the at least one power parameter and ultimately the plasma performance.

According to a further development of the invention, it is provided that a capacitor is used as the electronic proxy structure. In this context, a capacitor is generally understood to mean an electronic structure that at least behaves capacitively, preferably substantially capacitively, preferably exclusively capacitively. At least one capacitor or a capacitor arrangement, particularly preferably precisely one capacitor, is particularly preferably used as the electronic proxy structure. It has been found that the use of a capacitor as an electronic proxy structure for the functional verification proposed here produces a particularly reliable conclusion about the actual plasma power of the electrode arrangement.

The capacitance of the electronic proxy structure—hereinafter referred to as proxy capacitance—is preferably greater, in particular very much greater, preferably by a factor of at least 500 to at most 2000, preferably of at least 750 to at most 1500, preferably of 1000, greater than the capacitance of the electrode arrangement during the plasma operation—hereinafter referred to as the arrangement capacitance.

The voltage $V_{proxy}$ is proportional to the plasma voltage $V_{plasma}$ in the following way:

$$V_{proxy} = \frac{c_a}{c_a + c_p} V_{plasma}, \tag{1}$$

where $C_p$ is the proxy capacitance and $C_a$ is the arrangement capacitance.

This is explained in more detail using a preferred embodiment:

(Beginning of the preferred embodiment.) The arrangement capacitance is preferably proportional to a total edge length L (sum of all edge lengths) of a structured electrode of the electrode arrangement, at the edges of which the plasma is generated, and is found as:

$$C_a = c_L \cdot L \tag{2}$$

with the proportionality factor $c_L$.

The arrangement capacitance is, for example, 109 pF, and the plasma voltage is 3.5 $kV_{pp}$ (peak to peak). Furthermore, the total edge length L is 72 cm. This means that $c_L = C_a / L = 1.51$—such a value is typical for SMD electrode arrangements, where $c_L$ is in the range of $1 < c_L < 2$.

For metrological reasons, a value for the proxy voltage of roughly 3 to 5 $V_{pp}$ is desirable. This results in a scaling (where $C_p >> C_a$):

$$C_p = \frac{c_L \cdot L}{V_{proxy}} V_{plasma}. \tag{3}$$

The value of the plasma voltage is known from the control voltage (typically several kV), as is the desired proxy voltage. $C_p$ can be determined for an electrode configuration, which is substantially specified by the total edge length L, and the type of electrode (e.g. SMD—which defines $c_L$).

For a preferred electrode arrangement, equation (3) yields a reference value for the proxy capacitance of $C_p = 100$ nF (with $V_{proxy} = 3.5$ $V_{pp}$ and $V_{plasma} = 3.5$ $kV_{pp}$). (End of the preferred embodiment.)

According to a further development of the invention, it is provided that at least one value of the proxy voltage is measured as the at least one power parameter at a specific phase angle of the control voltage, in particular when the control voltage crosses zero. A mean value PM of the proxy voltage at the determined phase angle of the control voltage, averaged over several, in particular a plurality of, periods of the control voltage, is preferably determined as the at least one power parameter:

$$PM = \frac{1}{n} \sum_{i=1}^{n} V_{proxy,i}(\varphi), \tag{4}$$

wherein, in equation (4), $V_{proxy,i}(\varphi)$ is the value of the proxy voltage at the fixed phase angle—in particular at the zero crossing—the control voltage is in the period i, and n is a number of the periods of the control voltage over which the averaging takes place. According to a preferred embodiment, n=256; according to another preferred embodiment, n can assume a different or greater value. For n=256, for a frequency of the control voltage of x kHz, the mean value of the proxy voltage measured continuously once in each period is calculated every 1/(4x) seconds, if all measurements take place consecutively in successive periods. Especially with high frequencies, a measurement is only possible in certain periods (e.g. every second or third period, etc.), or it is necessary to measure every 256 periods one after the other and then leave a gap of a certain number of periods. The corresponding procedure must of course be taken into account to determine the plasma dose.

An assignment of the power parameter to the actual plasma power is preferably stored in a control device for controlling the electrode arrangement, preferably as a simple factor or as a more complex, preferably at least injective, preferably bijective function that unambiguously assigns an actual plasma power to a measured value of the power parameter.

According to a development of the invention, it is provided that the power parameter is compared with a first, upper target parameter value and with a second, lower target parameter value. The first, upper target parameter value is greater than the second, lower target parameter value. The at least one action is selected depending on whether the power parameter value falls within a target parameter range delimited by the first target parameter value and the second target parameter value. The first target parameter value and the second target parameter value thus delimit a target parameter range in which the power parameter is intended to fall; this means that the electrode arrangement is functioning properly if the power parameter falls within the target parameter range.

If, on the other hand, the power parameter is lower than the second, lower target parameter value or greater than the first, upper target parameter value, the electrode arrangement is not functioning properly and can either not be used or can only be used to a limited extent. The at least one action can in particular also be selected depending on how far the power parameter is from the first, upper target parameter value or from the second, lower target parameter value—outside the target parameter range. In particular, it is possible to separate an area for a yellow alarm and an area for a red alarm by means of corresponding further limit values.

The first, upper target parameter value takes into account an upper power limit for plasma generation, this upper power limit being exceeded, for example, by erosion of a dielectric of the electrode arrangement, deposition on the dielectric, leakage current formation or other similar effects that increase the power consumption of the electrode arrangement. The lower, second target parameter value takes into account a lower performance limit of the electrode arrangement, which can be exceeded, for example, through contamination, deposition and/or erosion of conductive components of an electrode of the electrode arrangement, or through other, similar effects that reduce the power consumption of the electrode arrangement.

According to a development of the invention, it is provided that the electrode arrangement is operated for a predetermined period of time before the at least one power parameter is determined. In this way, it can be ensured that constant operating conditions and/or an equilibrium for the operation of the electrode arrangement has/have been established, such that the power parameter is also correctly captured with respect to the continuous operation of the electrode arrangement.

The electrode arrangement is preferably operated for a first predetermined period of time before a first determination of the at least one power parameter. The functional verification is then carried out with the first determination of the at least one power parameter. If the result is positive, the plasma device can be used. If the result is negative, the electrode arrangement is operated for a second predetermined period of time. A new functional verification is then carried out. This procedure can be continued until either the functional verification delivers a positive result or a predetermined threshold number of repetitions has been reached or exceeded, or a predetermined maximum test period has expired, wherein a final decision is then made about the functionality of the electrode arrangement or the plasma device. The first predetermined time period, the second predetermined time period and optionally further predetermined time periods can have the same or different values, for example 15 seconds.

According to a further development of the invention, it is provided that the comparison result and/or the at least one power parameter is/are logged in an electronic storage device for later retrieval. The electronic storage device can be integrated directly into a control device for controlling the electrode arrangement, or can also be provided externally for this purpose. In particular, it is possible for the logging to take place in an external service provider which is operatively connected to the control device for the electrode arrangement via a wired or wireless data connection, for example WLAN and/or Bluetooth. Particularly preferably, the comparison result and/or the at least one power parameter is/are automatically logged, and/or particularly preferably is/are linked to at least one metadata item, for example a time stamp, information about a location of the use of the electrode arrangement, information about a purpose or a type of use of the electrode arrangement, information about certain parameters of the operation of the electrode arrangement, or the like. In this way, a logbook for the operation of the plasma device can be created so that its functionality and readiness for use, and/or its operation in general, can be traced over time.

It is preferably also possible to remotely monitor, read, and/or control the plasma device via a wired or wireless active connection, in particular a radio connection, preferably WLAN and/or Bluetooth, particularly preferably via Internet access and/or via a smartphone app.

The invention is explained in more detail below with reference to the drawings, in which.

Figure 1:
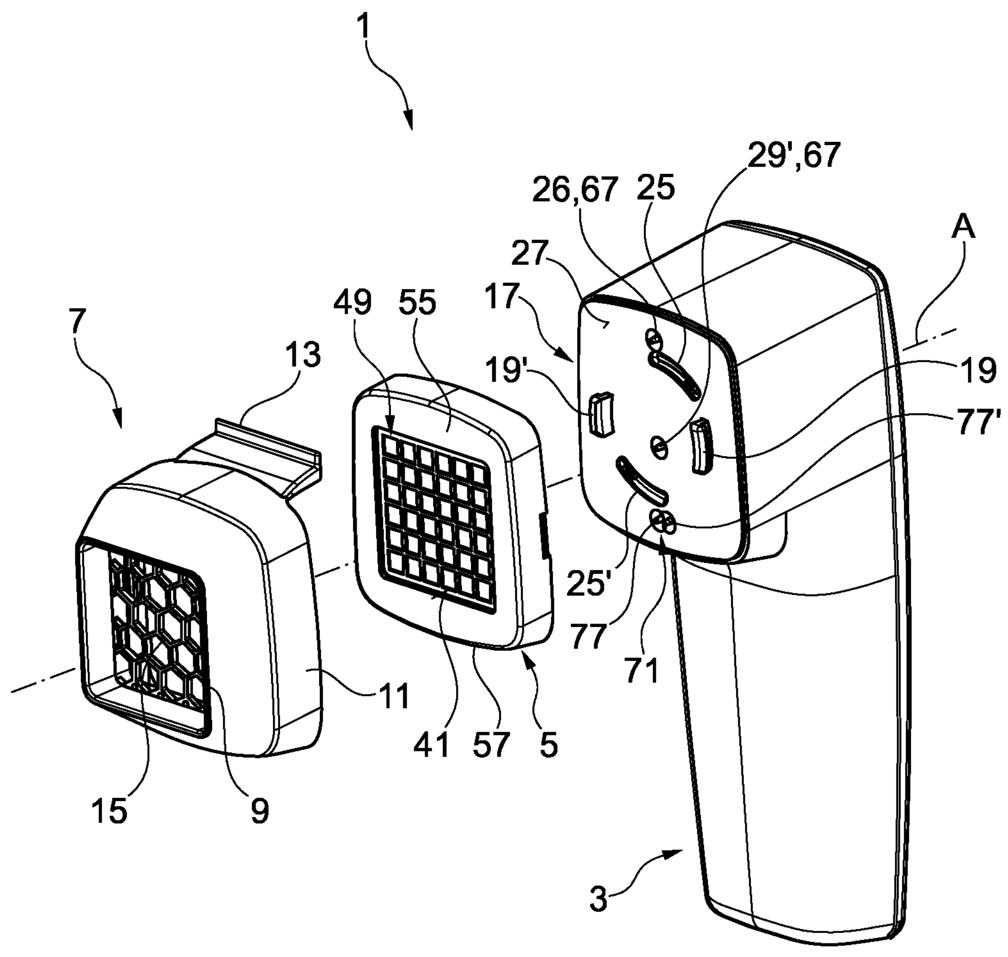
FIG. 1 is an exploded view of an embodiment of the plasma device from a first direction of view.

FIG. 1 shows an exploded view of an embodiment of a plasma device 1 for treating body surfaces, in particular skin surfaces, particularly preferably wounds. The plasma device 1 has a hand-held main body 3 on which a plasma source 5 is arranged. The plasma source 5 is detachably connectable to the main body 3, preferably connected, wherein the exploded view of FIG. 1 shows it in the state detached from the main body 3.

The plasma source 5 is configured for generating a non-thermal plasma.

The plasma device 1 also has a spacer 7 which is configured in the assembled state to define a distance between the plasma source 5 and a body treatment surface, which is not shown. The spacer 7 is detachably connectable, and preferably connected, to the main body 3 and/or the plasma source 5.

In this way, a possibility is created of using a suitable spacer 7 together with the plasma source 5 and the main body 3 for each treatment and, in particular, of exchanging the spacers 7 when different treatments are to be carried out. Furthermore, the spacer 7 can advantageously be designed as a single-use part or a disposable part which is disposed of after a body surface has been treated. No complex cleaning, disinfection or sterilization of the spacer 7 is then required, and the plasma device 1 can be operated very hygienically and at the same time simply and inexpensively.

The spacer 7 preferably has a circumferential edge 9 which, together with the body treatment surface and the plasma source 5, encloses a closed treatment volume.

The spacer 7 also has a circumferential collar 11 which, in the assembled state, overlaps the plasma source 5 and partially overlaps the main body 3. In this case, especially with the non-circular cross-sectional geometry of the plasma source 5 and the main body 3 in the region of the plasma source 5, the collar 11 provides anti-twist protection for the spacer 7, while at the same time preventing accidental detachment of the plasma source 5, which is detachably arranged on the main body 3, from the main body 3, by overlapping both elements. In particular, if the plasma source 5 is attached to the main body 3 by means of a plug-and-turn mechanism, it cannot be released because the collar 11 prevents the plasma source 5 from rotating relative to the main body 3.

The spacer 7 has a tab 13 which extends from the circumferential edge 9 or from the circumferential collar 11 in the direction of the plasma source 5 and the main body 3, and as such in the proximal direction, which is used to detach the spacer 7 from the main body 3 and/or the plasma source 5 is configured to. In particular, the tab 13 can be easily pushed from behind by a user of the plasma device 1, in particular with a finger of the same hand that also holds the main body 3, whereupon the spacer 7 can be easily detached from the plasma source 5 and the main body 3 and disposed of. In particular, there is no need to engage the plasma device 1 with both hands, which is favorable in particular with regard to the risk of contamination.

The spacer 7 preferably has a blocking element 15 which is permeable to non-thermal plasma, although it is designed to prevent contact, when installed on the main body 3 and/or the plasma source 5, of the treated body surface—or other body parts—with the plasma source 5. The blocking element 15 is designed as a grid in the embodiment shown here. Alternatively, it can also be designed as a mesh, as an arrangement of struts or bars, or in another suitable manner.

The plasma source 5 is preferably detachably connectable, in particular connected, to the main body 3 via a connecting device 17, wherein only the part of the connecting device 17 assigned to the main body 3 can be seen in FIG. 1, because a part of the connecting device 17 which is assigned to the plasma source 5 is covered by the plasma source 5.

The connecting device 17 has in particular a plug-and-turn mechanism, which is preferably designed in the manner of a bayonet lock. In this case, the plasma source 5 can preferably be placed on the main body 3 along an imaginary axis A in a specific angular position about the imaginary axis A, and then rotated about the imaginary axis A so that it is attached to the main body 3, in particular locked.

Figure 2:
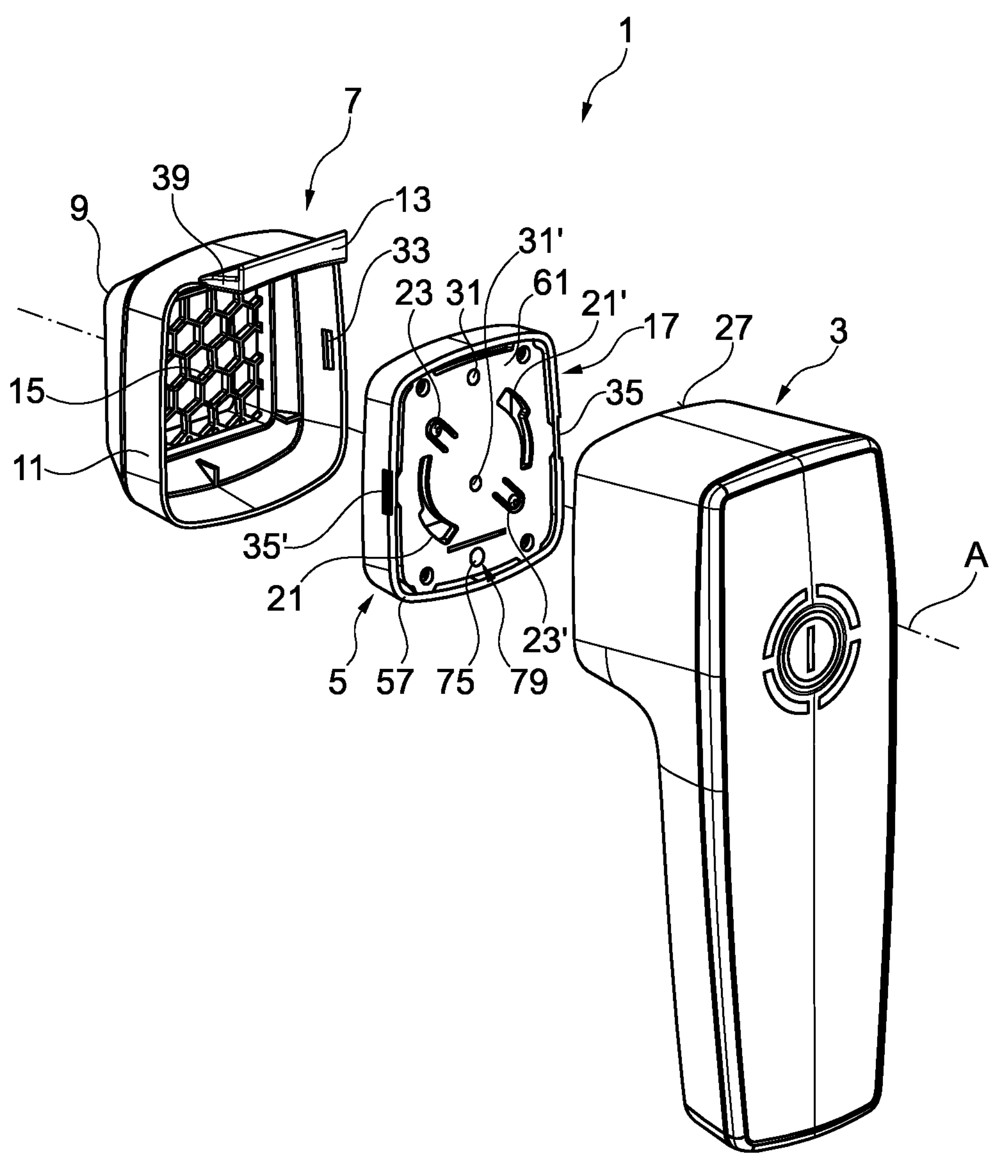
FIG. 2 is an exploded view of the embodiment of the plasma device according to FIG. 1, from a second direction of view.

The connecting device 17 in this case has two hook-shaped projections 19, 19' on the main body 3, which can be inserted into complementarily formed plug-and-turn recesses 21, 21' shown in FIG. 2, wherein the plasma source 5 can then be clamped in place with the main body 3 by a rotation about the imaginary axis A. In a manner known per se, the hook-shaped projections 19, 19' can be inserted into the plug-and-turn recesses 21, 21' in a certain first angular position of the plasma source 5 about the axis A, and then, after the plasma source 5 is rotated around the imaginary axis A, can engage behind the plug-and-turn recesses 21, 21' in another, second angular position in such a way that they can no longer be pulled out of the plug-and-turn recesses 21, 21'. Instead, this can only take place when the plasma source 5 has been rotated back into its first angular position about the imaginary axis A.

The connecting device 17 is preferably designed asymmetrically in such a way that the plasma source 5 can only be attached to the main body 3 in a specific orientation—in particular only in a specific angular position about the imaginary axis A. Here, in particular, the projections 19, 19' and the plug-and-turn recesses 21, 21' are designed asymmetrically, that is, differently, in particular with different sizes, such that at least the larger of the projections 19, 19' can only be inserted into the larger of the two plug-and-turn recesses 21, 21'. In this case, in particular a first projection 19 of the projections 19, 19' is made larger than a second projection 19' of the projections 19, 19'. Correspondingly, a first plug-and-turn recess 21 is designed larger than a second plug-and-turn recess 21' of the plug-and-turn recesses 21, 21'.

In addition, the connecting device 17, in this case on the plasma source 5, has at least one elastic projection 23, in this case preferably two elastically displaceable projections 23, 23', which in the assembled state each engage in a complementarily designed and arranged recess 25, 25' of the main body 3. There can also be more than two elastic projections 23, 23' and corresponding recesses 25, 25'. The projections 23, 23' and recesses 25, 25' preferably provide a pretension for the plasma source 5 on the main body 3 in the installed position and/or in the plug-on position. Such projections 23, 23' and recesses 25, 25' can, however, additionally or alternatively also be used in principle to ensure correct orientation of the plasma source 5 on the main body 3, in particular if they are designed and/or arranged asymmetrically.

Two contact pins 29, 29', which are configured for contacting the plasma source 5, can be seen in FIG. 1 on an end face 27 of the base body 3 on which the plasma source 5 rests when in the installed state, and on which the connecting device 17 is arranged with its elements which face the main body. In FIG. 2, it can be seen that the plasma source 5 has corresponding, complementary contacting recesses 31, 31', into which the contact pins 29, 29' engage when in the installed state, in order to make electrical contact with the plasma source 5. Instead of contacting recesses, contact surfaces or the like can also be provided.

FIG. 2 shows a further exploded view of the exemplary embodiment of the plasma device 1, from a different direction of view. Identical and functionally identical elements are provided with the same reference symbols, such that in this respect reference is made to the preceding description. It can be seen from FIG. 2 that the spacer 7 has at least one first snap-on element, preferably two first snap-on elements, of which only one first snap-on element 33 can be seen here. Another first snap-on element is preferably arranged on the side which is opposite the first snap-on element 33 when viewed in relation to a center plane of the plasma device 1, and is therefore covered in FIG. 2. The plasma source 5 in this case has at least one second snap-on element, preferably exactly two second snap-on elements 35, 35', the first snap-on elements 33 and the second snap-on elements 35 being matched to each other in such a manner that the first snap-on elements 33 and the second snap-on elements 35 can work together to hold the spacer 7 on the plasma source 5. The second snap-on elements 35, 35' can alternatively also be provided on the main body 3.

The first locking elements 33 are designed in this case as projections or undercuts, wherein the second locking elements 35, 35' are designed as recesses into which the first locking elements 33 can engage in a locking manner.

The spacer 7 preferably has an electronic identification device which can preferably be read without contact. The electronic identification device is particularly preferably designed as an RFID label. In this way, the spacer 7 can be identified by a control device 37 of the plasma device 1 shown in FIG. 3.

The electronic identification device is preferably integrated into the tab 13, particularly preferably received in a receiving recess 39 of the tab 13. In addition, it is preferably provided that a primary plane of the electronic identification device is oriented perpendicular to an electrode surface 41—see FIGS. 1 and 3—and thus at the same time also perpendicular to the end face 27. This allows the electronic identification device to be read in a contactless manner, even when the plasma source 5 is in operation, without the occurrence of relevant electromagnetic interference.

Figures 3, 4:
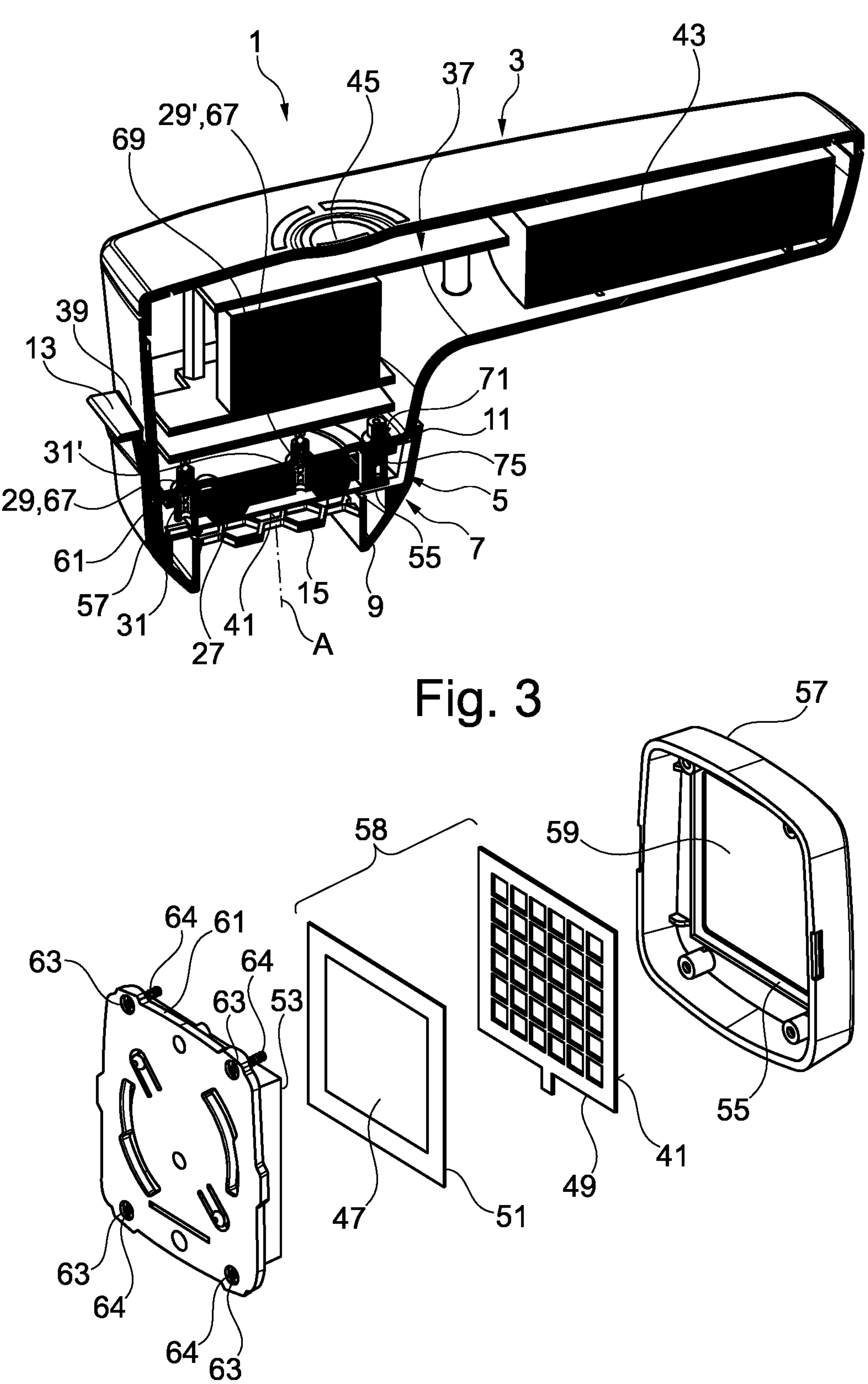
FIG. 3 is a sectional view of the embodiment of the assembled plasma device according to FIGS. 1 and 2.
FIG. 4 is an exploded view of the plasma source of the embodiment of the plasma device according to FIGS. 1 to 3.

FIG. 3 shows a schematic sectional illustration of the exemplary embodiment of the plasma device 1 according to FIGS. 1 and 2. Identical and functionally identical elements are provided with the same reference symbols, such that in this respect reference is made to the preceding description.

In FIG. 3, it can be seen in particular that the spacer 7 with the collar 11, when installed, not only overlaps the plasma source 5, but also partially overlaps the main body 3. It can also be seen that the plasma source 5, when installed, rests on the end face 27, wherein the contact pins 29, 29' engage in the contacting recesses 31, 31' or rest against contact surfaces.

The plasma device 1 is preferably designed to be battery-operated or accumulator-operated and to this extent has an electrical storage device 43 for storing electrical energy. The electrical storage device 43 is preferably designed as a battery or accumulator. It serves in particular to supply the plasma source 5—in particular via the contact pins 29, 29'—and the control device 37 with electrical power. The control device 37 is configured in particular to operate the plasma source 5 on the one hand and to read the electronic identification device of the spacer 7 on the other hand, and preferably to identify the spacer 7. The control device 37 is preferably further configured to only allow a single use of the same spacer 7. In particular, it is possible for the control device 37 to block or prevent operation of the plasma source 5 when it detects that no spacer 7 is present or that a spacer 7 that has already been used will be used again.

In this case, the control device 37 can also be configured to output an error message, an alarm or some other suitable message to a user of the plasma device 1.

The plasma device 1 also preferably has a charging station, which is not shown in the figures, in which the main body 3 can be inserted in order to charge the electrical storage device 43. In particular, the main body 3 can then be moved completely independently of other devices, in particular wirelessly, such that the operation of the plasma device 1 and the treatment of a body surface with the plasma device 1 is particularly simple.

A control element 45 can also be seen, which is arranged on the main body 3 in such a way that it can be operated simply and easily by a user of the plasma device 1, in particular by a thumb of the user's hand holding the main body 3. The operating element 45 is preferably designed as a button, push button, touch sensor, or in another suitable manner. An operating concept for the plasma device 1, which is implemented in particular in the control device 37, preferably follows a one-button operation in which at least all basic functions of the plasma device 1 can be selected and/or activated and/or operated by operating the one operating element 45. Of course, it is alternatively also possible for the plasma device 1 to have a plurality of operating elements. It is also possible for the plasma device 1 to have a display device, in particular integrated into the main body 3, wherein the display device is configured particularly to display parameters of the plasma device 1, and preferably in particular to be able to display various menus, in particular context menus, wherein the operating element 45 can change its function depending on the menu or context menu shown on the display device. The display device can also be designed as a touchscreen.

FIG. 4 shows an exploded view of the plasma source 5 of the exemplary embodiment of the plasma device 1 according to FIGS. 1 to 3. Identical and functionally identical elements are provided with the same reference symbols, such that in this respect reference is made to the preceding description.

The plasma source 5 is preferably configured for generating surface micro-discharges in ambient air on the electrode surface 41, which is at the same time a discharge surface of the plasma source 5 and thus a plasma generation surface. The plasma source 5 has a first planar electrode 47 and a second planar electrode 49 which, when installed, are spaced apart by a dielectric 51, wherein the two electrodes 47, 49 are in direct mechanical contact with the dielectric 51—but arranged on different sides thereof. In particular, they preferably lie against the dielectric 51 or are embedded into it. In the exemplary embodiment shown here, the first electrode 47 is preferably coated onto the dielectric 51, and the second electrode 49 is placed on the dielectric 51.

A potential difference, in particular an alternating voltage, is preferably applied to the electrodes 47, 49 via the contact pins 29, 29' in order to generate the non-thermal plasma on the electrode surface 41, and consequently on the discharge surface.

While the first electrode 47 is formed over the entire surface, the second electrode 49 is preferably structured, in this case in particular formed as a grid electrode. It has a plurality of edges at which the surface micro-discharges are ignited, wherein the non-thermal plasma is also formed at the edges of the second electrode 49.

The first electrode 47 is preferably energized with high voltage during operation of the plasma source 5, while the second electrode 49, which is arranged distally and thus facing the body treatment surface, is connected to ground or grounded. This increases the electrical safety of the operation of the plasma device 1.

In the exemplary embodiment shown here, the first electrode 47 and the dielectric 51, on the one hand, and the second electrode 49, on the other hand, are pressed against each other when in the installed state by a pressing element 53, and at the same time against a wall 55 of the plasma source 5. The wall 55 is preferably a wall of a housing 57 of the plasma source 5. In particular, it has a passage recess 59 for passage of the plasma generated on the electrode surface 41, the second electrode 49 in particular being pressed against an edge of the wall 55 in this respect.

By means of the pressing element 53, the first electrode 47, the dielectric 51 and the second electrode 49 are pressed against each other tightly and preferably without an air gap when in the assembled state, such that a highly efficient generation of a non-thermal plasma at the second electrode 49 is possible.

The pressing element 53 preferably has a circumferential pressure collar which is configured and adapted to the size of the dielectric 51 in order to apply a pressing force along an outer edge of the dielectric 51. In addition, the pressing element 53 preferably has at least one internal, in particular centrally arranged, pressure web or a plurality of preferably symmetrically, eccentrically arranged, pressure webs which are configured to apply pressing forces to the first electrode 47 and the dielectric 51 in an inner region. Damage to the dielectric 51, in particular, can preferably be avoided by means of the at least one pressure web; such damage may possibly be an issue if pressing forces were only introduced into the typically brittle dielectric 51 on the edge side. The electrode arrangement 58 comprising the first electrode 47, the dielectric 51 and the second electrode 49, and preferably also the pressing element 53, is arranged in the housing 57 when in the assembled state. At least the electrode arrangement 58 is preferably sealed in the housing 57. This allows a particularly simple cleaning and/or sterilization and/or disinfection of the plasma source 5 when it is detached from the main body 3. In particular, it is possible to clean the plasma source 5 in a water bath or ultrasound bath without its electrical operation or electrical safety being compromised.

On a side facing the end face 27 of the main body 3, in the assembled state, the housing 57 is closed by a cover element 61, which is preferably screwed to the housing 57.

In this respect, screw bores 63 and screws 64 with which the cover element 61 can be screwed onto the housing 57 are shown schematically here.

The cover element 61 and the pressing element 53 are formed in one piece with each other in the exemplary embodiment shown here.

It is important that when a body surface is treated, both electrodes 47, 49 are arranged on the same side of the body surface, the body surface in particular not being arranged between the electrodes, and the body surface not itself representing a counter electrode for a plasma electrode of the plasma source 5. In this way, a stable, reproducible non-thermal plasma with predetermined properties for treating the body surface can be generated.

Figure 5:
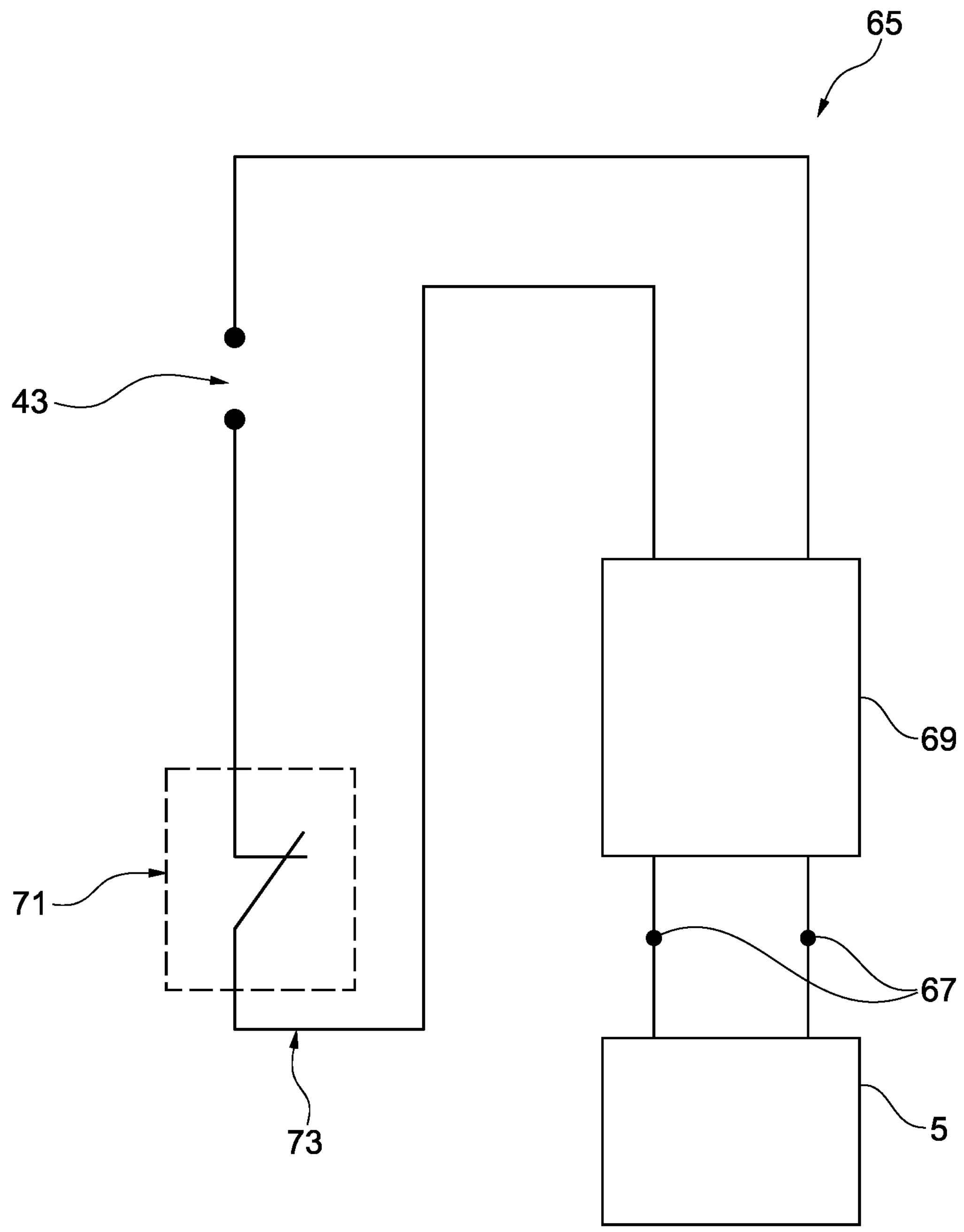
FIG. 5 is a schematic representation of an embodiment of a safety circuit for the plasma device.

FIG. 5 shows a schematic illustration of an exemplary embodiment of a safety circuit 65 for the plasma device 1.

The safety circuit 65 is configured to de-energize and/or break the flow of current to an electrical contact 67 which is configured for the electrical connection of the plasma source 5 with a high-voltage source 69 arranged in the main body 3, and which is implemented in this case by the contact pins 29, 29', if the plasma source 5 is detached from the main body 3, and is configured to allow the electrical contact 67 to be energized with voltage and/or current only when the plasma source 5 is arranged on the main body 3. The high voltage source 69 is also shown in FIG. 3. It is operatively connected to the control device 37 so that the control device 37 can control the high-voltage source 69.

As shown in FIGS. 1 to 3, the safety circuit 65 has a break 71 in an electrical supply line 73 from the electrical storage device 43 to the high voltage source 69 on the end face 27 of the main body 3. The plasma source 5 has a bridging contact 75 facing the end face 27 when in the installed state on the main body 3, which bridging contact is configured and arranged to electrically bridge the break 71 when the plasma source 5 is arranged on the main body 3. If, on the other hand, the plasma source 5 is separated from the main body 3, the electrical supply line 73 to the high-voltage source 69 is interrupted so that it is not supplied with electrical power. In this case, the electrical contact 67 for the plasma source 5 is therefore without current and/or voltage.

The break 71—as shown in FIG. 1—has two safety contact pins 77, 77' particularly on the end face 27, which are electrically isolated from each other and spatially distanced from each other. The bridging contact 75 is preferably configured to electrically connect the safety contact pins 77, 77' to each other when the plasma source 5 is arranged on the main body 3. The bridging contact 75 is preferably designed as a contact plate 79 or the like.

The safety mechanism of the safety circuit 65 is thus mechanically implemented here by two additional contacts in the form of the safety contact pins 77, 77' on the main body 3 and a shared counter contact on the plasma source 5 in the form of the bridging contact 75. If the plasma source 5 is separated from the main body 3, the break 71 is opened and thus the high-voltage source 69 is separated from the electrical storage device 43. The contact pins 29, 29' are then de-energized, with no current or voltage, such that no high voltage is applied in the region of the end face 27 accessible to a user. The safety mechanism is designed in this case in particular as a mechanical safety switch.

Figure 6:
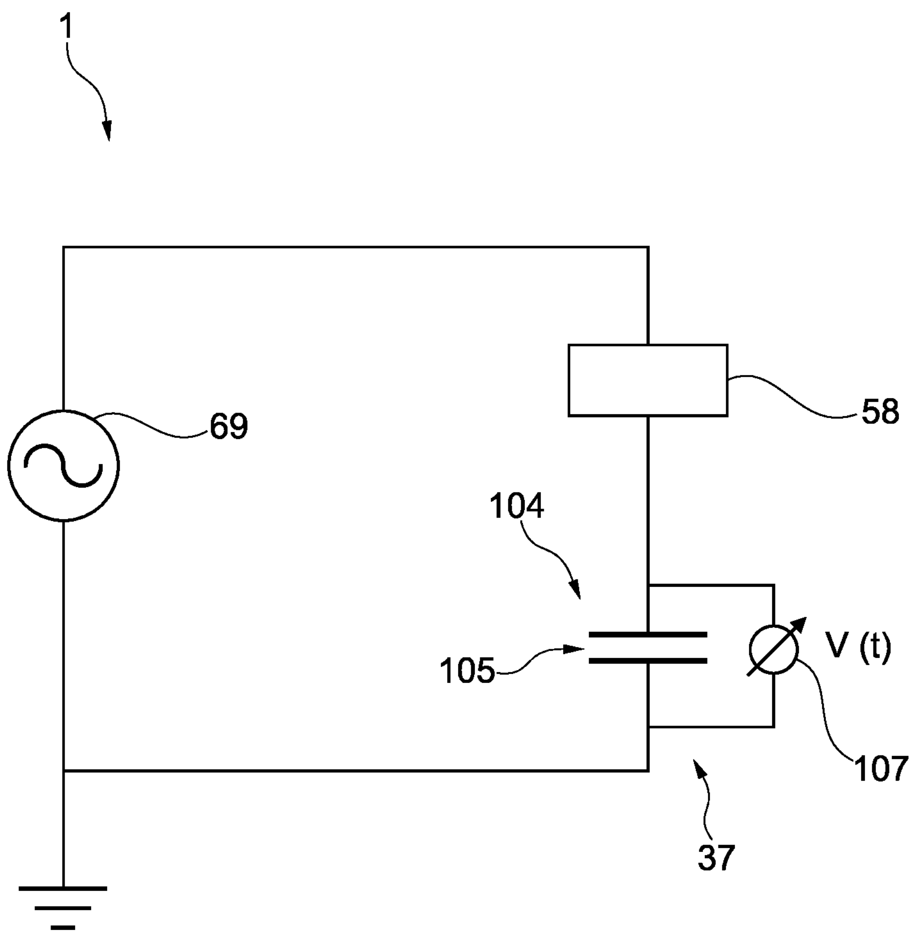
FIG. 6 is a schematic representation of a circuit diagram for performing a functional verification for the plasma device.

FIG. 6 shows a schematic representation of a circuit diagram for performing a functional verification for the plasma device 1. Identical and functionally identical elements are provided with the same reference symbols, such that in this respect reference is made to the preceding description.

The plasma device 1 has an electronic proxy structure 104 which is connectable in series with the electrode arrangement 58, and here is connected. The control device 37 is configured to detect the at least one power parameter on the electronic proxy structure 104 connected in series with the electrode arrangement 58. The electronic proxy structure 104 is particularly embodied in this case as a capacitor 105.

At least one value, in particular a mean value, of an alternating voltage V(t)—the proxy voltage—falling across the electronic proxy structure 104 at a certain phase angle of the control voltage generated by the high-voltage source 69, is measured as a power parameter, in particular averaged over a plurality of periods of the control voltage, especially according to equation (4) given above.

The proxy voltage is preferably detected as a function of time by a voltage measuring device 107.

The power parameter is preferably compared with a first, upper target parameter value and a second, lower target parameter value, wherein the at least one action is selected depending on whether the at least one power parameter falls into a target parameter range which is delimited by the first target parameter value and the second target parameter value.

A preclinical study was carried out with the plasma source 5 in order to determine a safe therapeutic window for treatments.

Initially, effectiveness studies were carried out. It was found that the plasma source 5 very effectively inactivates bacteria—including multi-resistant germs—and fungi. High reductions of four to five orders of magnitude are achieved in this case, within a treatment duration of only 60 seconds.

Further research showed that bacterial biofilms can also be inactivated. Reductions of three orders of magnitude were achieved within 60 seconds of treatment. A complete reduction could be achieved after a treatment time of 10 minutes.

Furthermore, safety investigations were carried out, in particular vitality studies on eukaryotic cells (primary fibroblasts and keratinocytes); mutagenicity tests; wound healing assays (to analyze the proliferation of cells), and examinations on ex vivo skin (histology, apoptosis or necrosis analysis).

These studies show that even in the worst case scenario of individual eukaryotic cells, there is no damage with treatment periods of up to 3 minutes. The mutagenicity tests did not show any induction of mutations for any plasma treatment duration (tested up to 5 minutes), and the ex vivo skin tests also showed no damage for any plasma treatment duration. This suggests an even larger therapeutic window than has been specified here.

The invention claimed is:

1. A plasma device (1) for treating body surfaces, having a main body (3) which is held in a hand, on which a plasma source (5) is arranged, which is configured for generating a non-thermal plasma, and having a spacer (7) which is physically disposed within a gap between the plasma source (5) and a body surface to be treated when in an installed state and while treating the body surface, wherein the body surface is distinct from the spacer (7), the spacer (7) constituting an element distinct from a first electrode (47), a second electrode (49), and a dielectric (51) of the plasma source (5), wherein the spacer (7) is detachably connected to the main body (3) and/or to the plasma source (5), wherein the plasma source (5) is detachably connected to the main body (3), the spacer (7) has at least one first snap-on element (33) and the plasma source (5) and/or the main body (3) has/have at least one second snap-on element (35, 35'), wherein the first snap-on element (33) and the second snap-on element (35, 35') are complementary to each other in such a manner that the first snap-on element (33) and the second snap-on element (35, 35') can work together to hold the spacer (7) on the main body (3) or the plasma source (5), and the spacer (7) has a tab (13) which extends from a circumferential edge (9) or from a circumferential collar (11), which in the installed state extends in the direction of the main body (3), and which is configured to detach the spacer (7) from the main body (3) or the plasma source (5).

2. The plasma device (1) according to claim 1, characterized in that the spacer (7) has the circumferential collar (11) which, in the installed state, overlaps the plasma source (5) and partially overlaps the main body (3).

3. The plasma device (1) according to claim 1 characterized in that the spacer (7) has an electronic identification device.

4. The plasma device (1) according to claim 1, characterized in that an electronic identification device is integrated into 1 tab (13), and/or in that a primary plane of the electronic identification device is perpendicular to an electrode surface (41) of the plasma source (5).

5. The plasma device (1) according to claim 1, characterized in that the plasma device (1) has a control device (37) which is configured to read an electronic identification device of the spacer (7).

6. The plasma device (1) according to claim 1, characterized in that the spacer (7) has a blocking element (15) which is permeable to non-thermal plasma, wherein the blocking element (15) is designed to prevent, in the installed state, contact of the treated body surface with the plasma source (5).

7. The plasma device (1) according to claim 1, characterized in that the plasma source (5) can be connected to the main body (3) via a connecting device (17), wherein the connecting device (17)

a) has a plug-and-turn mechanism, and/or b) is designed asymmetrically in such a way that the plasma source (5) can only be attached to the main body (3) in a certain orientation.

8. The plasma device (1) according to claim 1, characterized in that the plasma source (5) is configured for generating surface micro-discharges in ambient air on a discharge surface of the plasma source (5).

9. The plasma device (1) according to claim 8, characterized in that the first electrode (47) and the dielectric (51) and/or the second electrode (49) and the dielectric (51) are pressed against each other by a pressing element (53).

10. The plasma device (1) according to claim 8, characterized in that an electrode arrangement (58) consisting of the first electrode (47), the dielectric (51) and the second electrode (49) is arranged in a housing (57) of the plasma source (5).

11. The plasma device (1) according to claim 1, characterized in that the plasma device (1) has a safety circuit (65) which is configured to de-energize or break the current to an electrical contact (67) of the plasma source (5) when the plasma source (5) is detached from the main body (3), and to allow the electrical contact (67) to be supplied with voltage and/or current only when the plasma source (5) is arranged on the main body (3).

12. The plasma device (1) according to claim 1, wherein the body surface comprises a human skin surface.

13. The plasma device (1) according to claim 1, wherein the spacer is not an electrode.

14. The plasma device (1) according to claim 1, wherein the spacer maintains a distance between a plasma-generating surface and the body surface to be treated.

* * * * *